United States Patent
Neuhann

[11] Patent Number: 6,162,248
[45] Date of Patent: Dec. 19, 2000

[54] INTRA-OCULAR LENS

[76] Inventor: Tobias Neuhann, Clemensstrasse 94, D-80331 Munich, Germany

[21] Appl. No.: 09/309,503

[22] Filed: May 11, 1999

[30] Foreign Application Priority Data

May 11, 1998 [DE] Germany .......................... 198 21 029
Nov. 9, 1998 [DE] Germany .......................... 198 51 478

[51] Int. Cl.⁷ ........................................ A61F 2/16
[52] U.S. Cl. ................. 623/6.11; 623/6.16; 623/6.39
[58] Field of Search .................... 623/6.11, 6.16, 623/6.38, 6.39, 6.4

[56] References Cited

U.S. PATENT DOCUMENTS

| | | | |
|---|---|---|---|
| 4,124,905 | 11/1978 | Clark | 623/6.38 |
| 4,172,297 | 10/1979 | Schlegel | 623/6.4 |
| 4,963,148 | 10/1990 | Sulc et al. | 623/6.39 |
| 5,171,320 | 12/1992 | Nishi et al. | 623/6.39 |
| 5,266,074 | 11/1993 | Nishi et al. | 623/6.39 |
| 5,275,624 | 1/1994 | Hara et al. | |
| 5,370,687 | 12/1994 | Poler | 623/6.16 |
| 5,476,512 | 12/1995 | Sarfarazi | 623/6.39 |

FOREIGN PATENT DOCUMENTS 40 30 899  4/1992  Germany .

*Primary Examiner*—Dinh X. Nguyen
*Attorney, Agent, or Firm*—Evenson, McKeown, Edwards & Lenahan, P.L.L.C.

[57] ABSTRACT

An intra-ocular lens can be implanted as a posterior chamber lens by way of its lens body in a capsule sack remaining in the eye after an extracapsular operation. An equatorial edge of the lens body has a surrounding concave profile which is open to the outside and is bounded by two profile edges. At least one of the profile edges acts as a mechanical barrier against fibrosis on the rear capsule.

6 Claims, 1 Drawing Sheet

INTRA-OCULAR LENS

BACKGROUND OF THE INVENTION

The present invention relates to an intra-ocular lens which can be implanted as a posterior-chamber lens with its lens body in a capsule sac which remains in the eye after an extracapsular operation.

During an extracapsular cataract operation, a round piece of the frontal lens capsule is removed and the core is expressed. By means of a suction-rinsing system, the remaining cortex of the lens is removed by suction from the posterior capsule which has remained intact. A posterior-chamber lens is then implanted as the intra-ocular lens at the point of the removed natural lens of the eye. By means of known haptic devices, such as elastic loops or the like, the implanted lens is supported in the capsular sac, particularly in the equator area of the capsule sac.

Cloudiness, which develops later, frequently occurs as a result of the formation of secondary cataracts or because of fibrosis. The fibrosis material is formed from epithelial cells which have remained in the equator area of the capsule sac. These cells endeavor to spread over the surface of the posterior capsule, which causes the clouding on the posterior capsule.

SUMMARY OF THE INVENTION

It is an object of the invention to provide an intra-ocular lens of the initially mentioned type by which secondary cataract formation or fibrosis on the posterior capsule is avoided.

In an intra-ocular lens of the initially mentioned type, this object is achieved according to the invention by providing the equatorial edge of the lens body with a surrounding concave profile which is open toward the outside and is bounded by two profile edges.

The profile edges are designed such that, in the implanted condition of the intra-ocular lens, both edges, or at least the rear profile edge, can be placed against the capsule sac areas adjacent to the capsule sac equator.

The profile edges, specifically a frontal profile edge and/or a rear profile edge, extend around the equator of the lens body and rest on both sides of the capsule sac equator on the capsule sack material. As a result, these edges form or this edge forms a barrier against spreading of the epithelial cells remaining in the capsule sac equator, particularly onto the surface of the posterior capsule. Epithelial cells which grow again in the equator of the capsule sac are caught by the concave edge design of the lens body and are prevented from spreading.

This results in the additional advantage of anchoring the lens in the edge area on the interior side of the capsule sac.

Advantageously, the surrounding concave edge profile of the lens body can form a holding device for additives which cause proliferation of the remaining epithelial cells.

BRIEF DESCRIPTION OF THE DRAWINGS

The invention will be described in detail by way of embodiments shown in the drawing figures.

DESCRIPTION OF THE PREFERRED EMBODIMENTS

Figure 1:
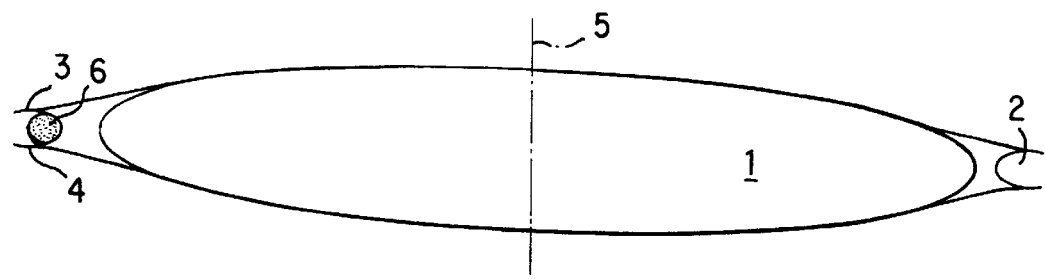
FIG. 1 is a view of a first embodiment.
Figure 2:
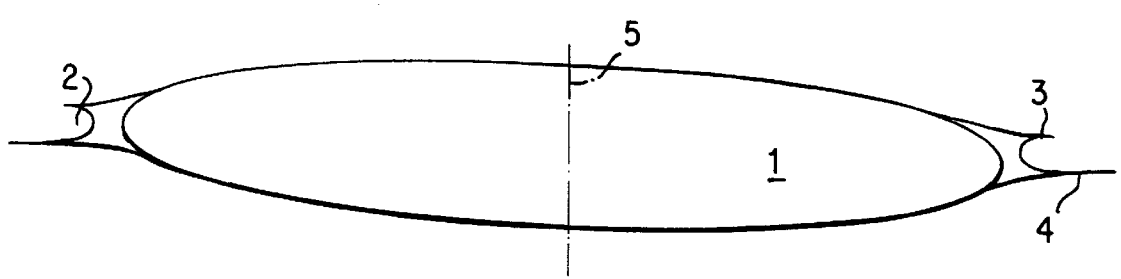
FIG. 2 is a view of a second embodiment.
Figure 3:
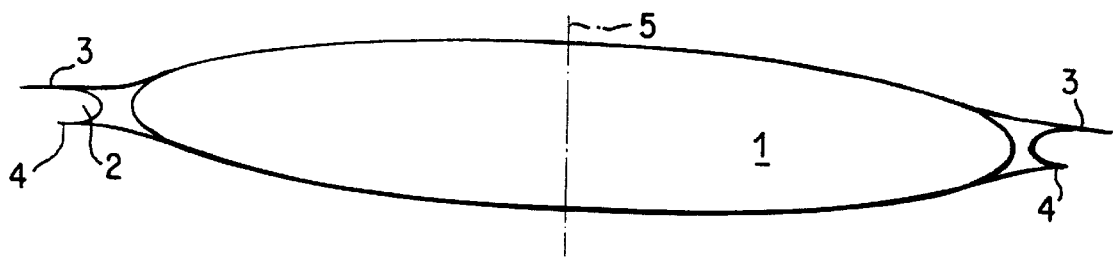
FIG. 3 is a view of a third embodiment.

The representations in FIGS. 1, 2 and 3 are meridian sectional views of the lens bodies of the various embodiments.

In the embodiments, the equatorial edges of a respective lens body 1 are shaped to a surrounding concave profile 2 which is open toward the outside. This concave edge profile 2 is bounded by two profile edges 3 and 4. In the embodiment of FIG. 1, the profile edges 3 and 4 have an equal radial distance from an optical lens axis 5 extending through the center of the lens body 1. In the embodiments of FIGS. 2 and 3, the profile edges 3 and 4 have different distances from the optical lens axis 5. In the embodiment of FIG. 2, the frontal profile edge 3 has a shorter distance from the optical lens axis 5 than the rear profile edge 4. In the embodiment of FIG. 3, the frontal profile edge 3 has a larger distance from the optical lens axis than the rear profile edge 4. In the implanted condition, the frontal profile edge 3 is situated closer to the frontal surface of the eye (surface of the cornea) than the rear profile edge 4.

The profile edges 2 can form holding devices for additives which, for example, hinder a cell growth (epithelial cell growth). The additives can be provided in a porous ring-shaped body 6 which is placed in the concave space of the profile 2 and extends along the whole equatorial edge of the lens body 1.

The profile edges 3 and 4, which taper starting from the lens body 1 and bound the concave profile 2, in the implanted condition of the lens body 1, rest against capsule sac areas which are adjacent to the capsule sac equator and are situated on both sides of the capsule sac equator. As a result, the profile edges 3 and 4, and particularly the rear profile edge 4, form a mechanical barrier against a growth of epithelial cells which proliferate particularly on the surface of the posterior capsule, which epithelial cells have remained behind in the area of the equator of the capsule sac during the extracapsular cataract operation. This prevents a capsule fibrosis on the posterior capsule and a resulting clouding of the rear capsule, particularly in the optically effective area of the lens body 1 behind the pupil of the eye. If a growth of residual epithelial cells occurs in the equator area of the capsule sac, then this growth is limited to the surrounding concave space of the edge profile 2 on the equator of the lens body 2.

In the embodiments illustrated in the figures, the surrounding concave profile which is open on the outside and which is shaped into the equatorial edge of the lens body has a curved boundary surface. Naturally, concave profiles can also be used which have linear boundary surfaces which meet in one or several corners in order to prevent proliferation of the epithelial cells which remained in the capsule sac equator.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Intra-ocular lens comprising a lens body which can be implanted as a posterior chamber lens in a capsule sac remaining in the eve after an extracapsular operation, the lens body including an equatorial edge which has a surrounding concave profile, said surrounding concave profile being open to the outside and bounded by two profile edges, wherein, of the two profile edges, in an implanted condition, at least a rear profile edge can be placed on the capsule sac area posterior of the capsule sac equator.

2. Intra-ocular lens according to claim 1, wherein the two profile edges have different radial distances from the optical lens axis.

3. Intra-ocular lens according to claim 2, wherein the surrounding concave profile forms a holding device for additives.

4. Intra-ocular lens according to claim 1, wherein the surrounding concave profile forms a holding device for additives.

5. Intra-ocular lens comprising a lens body which can be implanted as a posterior chamber lens in a capsule sac remaining in the eye after an extracapsular operation, the lens body including an equatorial edge which has a surrounding concave profile, said surrounding concave profile being open to the outside and bounded by two profile edges, wherein, of the two profile edges, in an implanted condition, a rear profile edge can be placed on the capsule sac area posterior of the capsule sac equator, and wherein said rear profile edges have a larger radial distance from the optical lens axis than the front profile edge.

6. Intra-ocular lens according to claim 5, wherein the surrounding concave profile forms a holding device for additives.

* * * * *